US00PP30406P3

(12) United States Plant Patent
Unger

(10) Patent No.: US PP30,406 P3
(45) Date of Patent: Apr. 16, 2019

(54) ***CUPHEA* PLANT NAMED 'WESCUFLODIA'**

(50) Latin Name: *Cuphea hyssopifolia*
Varietal Denomination: Wescuflodia

(71) Applicant: IP Improved Products by Breeding UG, Worms (DE)

(72) Inventor: Helmut Unger, Worms (DE)

(73) Assignee: IP Improved Products by Breeding UG, Worms (DE)

( * ) Notice: Subject to any disclaimer, the term of this patent is extended or adjusted under 35 U.S.C. 154(b) by 0 days.

(21) Appl. No.: 15/932,134

(22) Filed: Feb. 7, 2018

(65) Prior Publication Data

US 2018/0228071 P1 Aug. 9, 2018

Related U.S. Application Data

(60) Provisional application No. 62/499,931, filed on Feb. 7, 2017.

(51) Int. Cl.
*A01H 5/02* (2018.01)
*A01H 6/00* (2018.01)

(52) U.S. Cl.
USPC ..... Plt./420
CPC ..... *A01H 6/00* (2018.05)

(58) Field of Classification Search
USPC ..... Plt./420
See application file for complete search history.

*Primary Examiner* — Annette H Para
(74) *Attorney, Agent, or Firm* — The Webb Law Firm

(57) ABSTRACT

A new and distinct *cuphea* plant having red-purple colored flowers.

1 Drawing Sheet

Botanical classification: *Cuphea hyssopifolia.*
Varietal denomination: 'Wescuflodia'.

BACKGROUND OF THE INVENTION

The present invention comprises a new and distinct cultivar of *cuphea* plant known by the varietal name 'Wescuflodia'. The new variety was discovered in June of 2015 in Worms, Germany as the result of a planned breeding program with the purposes of providing *cuphea* plants with improved growing characteristics and better garden performance. The new variety is the result of a mutation of a *Cuphea hyssopifolia* variety from the breeder's proprietary collected referred to as UNGCU15 (unpatented). The new variety is similar to UNGCU15 in flower color, but exhibits earlier development, a more compact habit, and larger flowers than UNGCU15. The first asexual reproduction of the new variety was conducted by cuttings in June of 2015 in Worms, Germany. 'Wescuflodia' has been trial and field tested and has been found to retain its distinctive characteristics and remain true to type through successive propagations. The present invention has not been evaluated under all possible environmental conditions. The phenotype may vary with variations in environment without a change in the genotype of the plant.

When 'Wescuflodia' is compared to *Cuphea hyssopifolia* 'Wescuflomig' (U.S. Plant patent application Ser. No. 15/932,131, filed on Feb. 7, 2018), the varieties are similar in plant form, branching habit, and leaf color. However, the varieties differ in flower color ('Wescuflomig' has pale pink colored flowers) and size, as well as anther number.

The following traits distinguish 'Wescuflodia' as a new and distinct cultivar from other *cuphea* varieties known to the breeder:

1. Flower size;
2. Flowering period;
3. Flower color; and
4. Growth habit.

DESCRIPTION OF THE DRAWING

The accompanying photographic drawing taken at approximately 11 months of age illustrates the new variety, with the colors being as nearly true as is possible with color illustrations of this type:

FIG. 1 illustrates an entire flowering plant of the new variety.

DESCRIPTION OF THE PLANT

The following detailed description sets forth the characteristics of the new variety at approximately 11 months of age. The data which defines these characteristics was collected indoors in Südlohn-Oeding, Germany under inflorescent light in the Winter. Plants of the new variety were grown in the Winter in Germany in a glass greenhouse under artificial light levels of 3,000 lx for 16 hours per day in 17.8 cm pots. Color references are primarily to the 2001 R.H.S. Colour Chart of The Royal Horticultural Society of London.

Plant:

*Number of days to initiate roots.*—About 20 days at an average of 20° C.

*Number of days to develop roots.*—About 30 days at an average of 20° C.

*Time to produce a finished, flowered plant from a rooted cutting.*—About 12 to 16 weeks in a 12 cm container.

*Rooting habit.*—Fibrous.

*Overall plant shape.*—Upright, mounded, and symmetrical.

*Plant height.*—Approximately 27 cm.

*Plant diameter.*—Approximately 43 cm.

*Plant vigor.*—Moderate.

*Branching.*—Habit: Moderate basal branching. Lateral branches: Length: 11 cm. Diameter: 0.2 cm. Internode length: 1 cm. Texture: Slightly rough with pubescence present. Color: 146D.

*Foliage.*—Appearance: Alternate. Number of leaves per branch: About 24, with indeterminate growth. Shape: Lanceolate. Apex: Acute. Base: Cuneate. Margin: Entire. Length: 3.7 cm. Width: 1.3 cm. Texture: Smooth. Aspect: Flat. Color: Young leaves: Upper surface: 137A. Lower surface: 138A. Mature leaves: Upper surface: 136B. Lower surface: 138A. Veins: Venation type: Pinnate. Color: One shade lighter than leaf color of respective maturity and surface. Petiole: Length: 0.4 cm. Diameter: Less than 0.1 cm. Color: 146D.

Flowers:

*Buds* (*described right before color is visible—petals not visible*).—

*Shape.*—Oblong.

*Diameter.*—0.15 cm.

*Length.*—0.5 cm.

*Color.*—145B at the top and 143C at the bottom.

*Flower.*—Natural flowering season: From April until October/frost in Germany. Flower type and habit: Single and continuous. Number of flowers per lateral branch: From 1 to 3 at a time, with indeterminate growth. Flower longevity: 2 to 5 days on the plant. Lastingness of a cut flower: Not applicable. Diameter: 1.7 cm. Height: 1.4 cm. Throat diameter: 0.2 cm.

*Corolla.*—Form: Actinomorphic and zygomorphic. Appearance: Smooth and crinkled. Petals/lobes: Number per flower: 6. Length: 0.8 cm. Width: 0.5 cm. Shape: Elliptic and fused with sepals. Apex: Obtuse. Base: Fused with sepals. Margin: Entire. Aspect: Flat and slightly incurved. Texture (both surfaces): Smooth and crinkled. Color: Upper surface (when opening): N74A. Lower surface (when opening): N74A. Upper surface (fully opened): N74A. Lower surface (fully opened): N74A. Throat: Texture: Smooth, with pubescence present at the upper end. Color: Greenish-cream. Tube color: N144C.

*Calyx.*—Form: Fused. Length: 0.6 cm. Diameter: 0.2 cm. Sepals: Fused to tube, having a smooth texture and color of N144D.

Reproductive organs:

*Stamens.*—Number (per flower): About 6. Filament: Length: Less than 0.5 cm. Anthers: Shape: Dorsifixed. Length: About 0.1 cm. Color: Grey. Pollen: Color: Grey. Amount (generally): Minimal.

*Pistils.*—Length: 0.3 cm. Style: Length: 0.3 cm. Color: White. Stigma: Shape: Thin. Color: White.

General:

*Disease/pest resistance or susceptibility.*—None observed.

*Cold temperature tolerance.*—Intolerant to frost.

*Fragrance.*—None observed.

*Seed production.*—Minimal.

I claim:

1. A new and distinct variety of *cuphea* plant, as is herein illustrated and described.

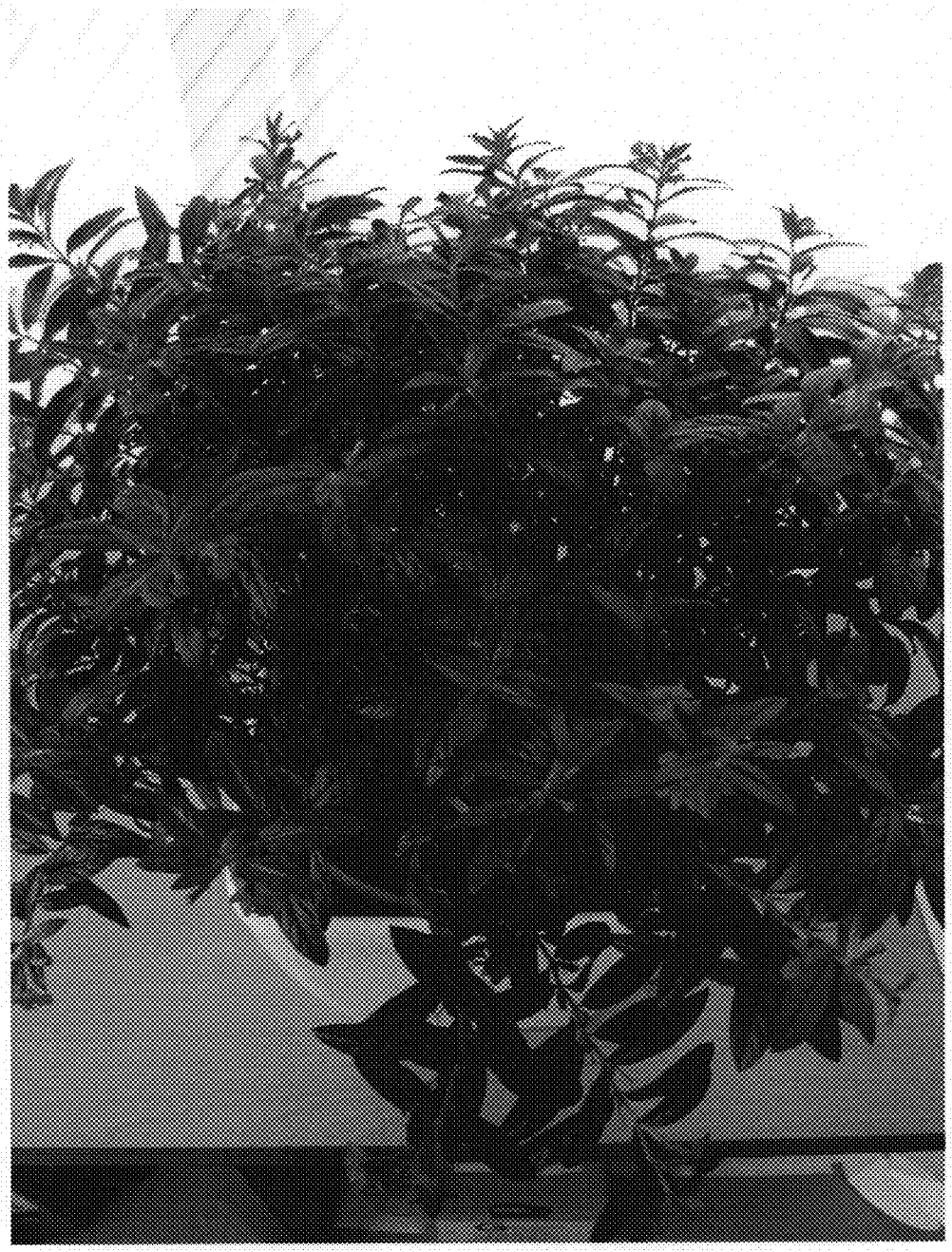

* * * * *